United States Patent [19]

Etzkorn et al.

[11] Patent Number: 5,243,082

[45] Date of Patent: Sep. 7, 1993

[54] PROCESS FOR IN-SITU PRODUCTION OF ACROLEIN

[75] Inventors: William G. Etzkorn, Hurricane; William D. Neilsen, South Charleston, both of W. Va.

[73] Assignee: Union Carbide Chemicals & Plastics Technology Corporation, Danbury, Conn.

[21] Appl. No.: 948,501

[22] Filed: Sep. 22, 1992

[51] Int. Cl.$^5$ ............................................... C07C 45/51
[52] U.S. Cl. .................................... 568/465; 568/484; 568/485; 568/459
[58] Field of Search ............... 568/458, 459, 465, 479, 568/484, 485

[56] References Cited

U.S. PATENT DOCUMENTS

| | | | |
|---|---|---|---|
| 2,562,849 | 7/1951 | Whetstone et al. | 260/486 |
| 2,577,445 | 12/1951 | Hortnick | 260/601 |
| 3,159,651 | 12/1964 | Johnson et al. | 260/345.9 |
| 3,380,462 | 4/1968 | Schieber et al. | 137/3 |
| 4,851,583 | 7/1989 | Bockowski et al. | 568/465 |
| 5,081,314 | 1/1992 | Kissel et al. | 568/479 |

OTHER PUBLICATIONS

"Acrolein" ed. by Smith, 1962 Wiley Co. Thermal Dimers by Fourie et al pp. 180–185 and 207.
"Acrolein" ed. by Smith, 1982 Wiley Co. Diels-alder Reaction by Smith pp. 214–215.

*Primary Examiner*—Werren B. Lone
*Attorney, Agent, or Firm*—J. F. Leightner

[57] ABSTRACT

Acrolein is prepared by the heating of 3,4-dihydro-2H-pyran-2-carboxaldehyde. The process provides acrolein in very high yields and with few impurities. The process is advantageously employed to produce acrolein at the point of use.

7 Claims, No Drawings

PROCESS FOR IN-SITU PRODUCTION OF ACROLEIN

FIELD OF THE INVENTION

This invention relates to the generation of acrolein. More particularly, this invention is directed to a process which can be used to generate acrolein for immediate use at a remote location.

BACKGROUND OF THE INVENTION

Acrolein is known to have unique properties and is reported to be an effective biocide, a sulfide scavenger in oil and gas wells and a herbicide, see for example, see U.S. Pat. Nos. 2,959,476, 3,250,667 and 5,081,314. Despite the many beneficial properties of acrolein, its use has been significantly limited due to its relatively high vapor pressure and acute toxicity. These properties and the limited quantities required for many applications has restricted the use of acrolein in many applications despite its reported efficacy.

In an effort to utilize the unique properties of acrolein, several attempts have been made to provide acrolein in limited quantities in a safe manner. A special system described in U.S. Pat. No. 3,380,462 (Schieber et al.) discloses an elaborate system to ensure safe generation of acrolein. However, this system designed to isolate acrolein and prevent its escape was plagued by the potential for accidental releases resulting in employee exposure and potential health effects.

U.S. Pat. No. 4,851,583 (Bockowski et al.) discloses a method of generating acrolein from the acetal of acrolein via exposure to a sulfonic acid reusable catalytic material. The acetal reacts with the acidic material to form acrolein and two moles of alcohol. While acrolein is generated in the process, undesirable levels of alcohol are also generated.

Despite these disclosures, a long-felt need still exists for a process which will safely generate high purity acrolein in sufficient quantity for various applications.

SUMMARY OF THE INVENTION

The present invention provides a process for the in-situ generation of acrolein from 3,4-dihydro-2H-pyran-2-carboxaldehyde (DPC). The process provides acrolein in very high yields and with few impurities.

DETAILED DESCRIPTION OF THE INVENTION

The invention relates to the generation of acrolein from 3,4-dihydro-2H-pyran-2-carboxaldehyde. DPC has the chemical structure given below in Formula I.

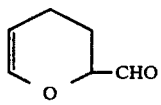

(I)

Production of DPC is described in U.S. Pat. No. 3,159,651 (Johnson et al.). Johnson et al. disclose that DPC is a highly reactive molecule that will polymerize with itself, with acrolein or substituted acroleins to form larger molecules or "heavies". These higher molecular weight materials are undesirable because these molecules do not have the same beneficial properties of acrolein in the various applications noted above.

It has been surprisingly discovered that DPC can be converted to acrolein and virtually no other by-products by heating DPC to a temperature from about 350 to about 650° C. Preferably the DPC is heated to a temperature ranging from about 375 to about 550° C and most preferably from about 400 to about 525° C. The simplicity of the process and the limited equipment required to convert DPC to acrolein allows this process to be carried out in remote locations.

The generation of acrolein from DPC can be conducted in either continuous or batch Processes. The amount of acrolein generated from the process is determined by, but not limited to, the reactor temperature, the residence time of DPC in the reactor and the feed rate of DPC to the reactor.

Residence time within the reactor can vary widely from about 0.01 to about 100 seconds. Generally the residence time is from about 0.1 to about 20 seconds and most preferably 0.5 to about 10 seconds.

Feed rates to the reactor vary according to the amount of acrolein required, the use of diluents and the size of the reactor. Feed rates should provide sufficient residence time so as to obtain adequate conversion of the DPC to acrolein.

After the DPC is converted to acrolein, it is advantageous to cool the acrolein quickly so as to minimize the formation of any by-products. Acrolein boils at 56° C. at atmospheric pressure. Generally, the acrolein is cooled to a temperature of from about 10 to about 50° C., preferably from about 15 to about 35° C. and most preferably, from about 20 to about 30° C. at atmospheric pressure. Those with skill in the art will readily appreciate that the acrolein can be condensed at higher temperatures if higher pressures are employed. The particular temperatures and pressures employed to condense the acrolein may vary widely without departing from the scope of the present invention. In a preferred embodiment of the present invention, the acrolein product is immediately condensed at atmospheric pressure as it exits the reactor.

The acrolein product is cooled by means well known in the art including, but not limited to, heat exchangers, jacketed tanks and tanks with internal cooling coils and baffles. Cooling media suitable for use in this invention includes cooling water, chilled water and brine.

The acrolein produced by the present method contains substantially no other materials other than unconverted DPC. Acrolein conversion exceeding 95 percent by weight is routinely achieved and conversion of greater than 99 percent is also achievable. As the reaction temperature approaches 500° C. the conversion of DPC to acrolein approaches 100 percent.

Another advantage of the present invention is the production of substantially anhydrous acrolein. Substantially anhydrous as used herein is defined to mean that there is less than 0.5 percent by weight water in the acrolein product. Unlike other processes in which acrolein must be separated from water, the conversion of DPC to acrolein does not create water as a by-product. Consequently, a separate drying step is not required to remove water from the acrolein product.

Product losses to polymerization are minimal and only minor efficiency losses due to charring and carbon formation are noted. Surprisingly, little or no polymer formation is noted in the process. Contrary to the suggestion of the prior art, it has been found that the conversion of DPC to acrolein can be conducted without the expected reaction of DPC with itself or acrolein to produce undesired by-products.

Various reactors designs may be employed to convert the DPC to acrolein. The reactor may be comprised of tubes, packed beds or columns, of which tubes are preferred. The tubes may be coiled or straight, of which, straight tubes are preferred. The reactor is constructed from materials suitable for the operating temperature stated above. Such materials include, but are not limited to, stainless steel, Hastalloy ® alloys, steel, titanium and high temperature glass of which stainless steel is preferred. The reactor may be also packed with beads or rings made from inert materials such as ceramics, glass and stainless steel. Diluents can also be added to the reactor, including, but not limited to cycloaliphatic hydrocarbons such as cyclohexane; aliphatic hydrocarbons such as hexane; aromatic hydrocarbons such as benzene; alcohols; nitrogen, water and mixtures thereof. Especially preferred diluents are nitrogen and water.

The present invention is advantageously employed in locations that do not require large quantities of acrolein or where storage and handling of acrolein is difficult. An advantage of the present invention is that the process can be designed to produce sufficient acrolein to fulfill the particular requirements of a given application. The acrolein is then directly consumed in remote locations where operations such as oil wells, waste water facilities and paper pulping plants are located. Since the acrolein is produced on an as needed basis there is no need to handle or store the acrolein product.

In contrast to acrolein, anhydrous DPC can be safely stored in remote locations for extended periods of time, especially if it is kept under a nitrogen blanket. DPC also has a lower vapor pressure than acrolein and is less toxic. Consequently, DPC is much easier to safely store and handle than acrolein and presents considerably less hazard in shipping.

Whereas, the exact scope of the present invention is set forth in the appended claims, the following specific examples illustrate certain aspects of the present invention and more particularly, point out methods of including the same. The examples are set forth for illustration only and are not to be construed as limitations on the present invention except as set forth in the appended claims. All parts and percentages are by weight unless otherwise specified.

EXAMPLE 1

DPC from a vented feed tank, 2 liters total volume was pumped to a coiled ⅜ inch stainless steel tubular reactor. A nitrogen source was also provided to the reactor inlet. The reactor had a total volume of 112 milliliters. The reactor was heated with a ceramic furnace. Flow from the reactor was passed through a water-cooled heat exchanger and cooled to less than 56° C. Flow was then conducted to a receiver which was immersed in a dry ice/acetone bath to recover the liquefied acrolein. The acrolein receiver was vented to remove nitrogen and non-condensable gases.

The reactor temperature, space velocity of the gas stream, feed composition and residence time of the gases were varied. Product analyses were performed by capillary gas chromatography utilizing a flame ionization detector and internal standard. The feed gas composition, space velocity, reactor temperature and results are presented in Table 1 below.

TABLE 1

| Temp. °C. | Space Velocity (hr$^{-1}$) | Feed, Mole % N$_2$ | DPC | H$_2$O | Residence Time (secs.) | Product Analysis (wt. %) Acrolein | DPC |
|---|---|---|---|---|---|---|---|
| 450 | 578 | 95.2 | 4.1 | — | 6.2 | 99.82 | 0.18 |
| 500 | 696 | 97.1 | 2.9 | — | 5.2 | 99.82 | 0.18 |
| 400 | 696 | 96 | 4 | — | 5.2 | 96.23 | 3.77 |
| 500 | 460 | 95.7 | 4.3 | — | 7.8 | 99.48 | 0.52 |
| 500 | 378 | 92.9 | 7.1 | — | 9.5 | 99.9 | 0.10 |
| 500 | 475 | 95 | 5 | — | 7.6 | 100 | — |
| 400 | 378 | 94.8 | 5.1 | — | 5.2 | 95.7 | 4.3 |
| 400 | 378 | 92.9 | 7.1 | — | 9.5 | 95.35 | 4.65 |
| 500 | 572 | 95.2 | 4.8 | — | 6.3 | 99.83 | 0.17 |
| 400 | 572 | 96.5 | 3.5 | — | 6.3 | 89.53 | 10.47 |
| 450 | 475 | 95 | 5 | — | 7.6 | 99.26 | 0.74 |
| 300 | 572 | 95.2 | 4.8 | — | 6.3 | 8.4 | 91.6 |
| 450 | 696 | 80 | 20 | — | 5.2 | 98.4 | 1.6 |
| 450 | 572 | 81 | 1 | 18 | 6.3 | 97.5 | 2.5 |

The above results demonstrate the efficacy of the present invention in producing high purity acrolein under a variety of conditions while utilizing both nitrogen and water as diluents.

EXAMPLE 2

In a second series of experiments, DPC was fed to a horizontal reactor which was thirty inches in length and six inches in diameter. Inside the reactor, four ⅝ inch stainless steel tubes were fixed within the reactor in a rectangular pattern. Each of the tubes was 1.5 inches from the outside surface of the reactor. The center of the tubes were three inches from the tube diagonally situated from it. The reactor was heated using four, 1000 watt electric band heaters wrapped vertically around the reactor.

Similar heat exchanger and product receiver apparatus were set up as described in Example 1 to recover the products from the reactor. Product analyses were once again performed by capillary gas chromatography utilizing a flame ionization detector and an internal standard.

The results are listed in Table 2 below.

TABLE 2

| Trial | Flow (ml/min.) | Temperature (°C.) | Acrolein (weight percent) | DPC (weight percent) |
|---|---|---|---|---|
| A | 13.2 | 483 | 89.65 | 10.4 |
| B | 20.5 | 476 | 73.9 | 26.1 |
| C | 40.0 | 465 | 47.0 | 53.0 |
| D | 4.9 | 501 | 99.3 | 0.7 |
| E | 4.9 | 500 | 99.6 | 0.4 |

At approximately 500° C. and the lowest flow rate, i.e., highest residence time in the reactor, the conversion of DPC to acrolein was almost complete (Trials D and E). At lower temperatures and higher flow rates, acrolein yield was greatly diminished (Trials A, B and C).

We claim:

1. A method for preparing acrolein which comprises heating 3,4-dihydro-2H-pyran-2-carboxaldehyde at a temperature from about 450° C. to about 500° C. for about 0.5 seconds to about 10 seconds wherein 3,4-dihydro-2-H-pyran-2-carboxaldehyde is converted to acrolein from about 99 to about 100 percent by weight.

2. The method of claim 1 wherein a diluent is added.

3. The method of claim 2 wherein the diluent is selected from the group consisting of water, nitrogen and mixtures thereof.

4. A method for preparing acrolein which comprises:

(a) heating 3,4-dihydro-2H-pyran-2-carboxyaldehyde to a temperature from about 450° C. to about 500° C. for about 0.5 to about 10 seconds to produce acrolein from about 99 percent to about 100 percent by weight; and (b) condensing the acrolein.

5. The method of claim 4 wherein nitrogen is added as a diluent.

6. The method of claim 4 wherein water is added as a diluent.

7. The method of claim 4 wherein the acrolein is condensed at a temperature of from about 10° to about 50° C.

* * * * *